United States Patent [19]
Rolland et al.

[11] Patent Number: 6,141,577
[45] Date of Patent: Oct. 31, 2000

[54] THREE DIMENSIONAL OPTICAL IMAGING COLPOSCOPY

[75] Inventors: Jannick P. Rolland, Chuluota; Peter J. Delfyett, Jr., Geneva, both of Fla.

[73] Assignee: University of Central Florida, Orlando, Fla.

[21] Appl. No.: 09/263,021

[22] Filed: Mar. 5, 1999

Related U.S. Application Data

[62] Division of application No. 09/002,069, Dec. 31, 1997, Pat. No. 5,921,926.
[60] Provisional application No. 60/053,960, Jul. 28, 1997.

[51] Int. Cl.[7] ................................................. A61B 5/00
[52] U.S. Cl. ........................... 600/407; 600/473; 600/478
[58] Field of Search ................................ 600/407, 476, 600/478, 473, 475; 356/300, 302, 303, 317, 318, 326, 345, 346; 250/338.1, 358.1, 363.02

[56] References Cited

U.S. PATENT DOCUMENTS

| | | | |
|---|---|---|---|
| 5,179,937 | 1/1993 | Lee | 128/17 |
| 5,321,501 | 6/1994 | Swanson | 356/345 |
| 5,451,785 | 9/1995 | Faris | 250/330 |
| 5,456,260 | 10/1995 | Kollias et al. | 600/478 |
| 5,458,595 | 10/1995 | Tadir | 606/15 |
| 5,465,147 | 11/1995 | Swanson | 356/345 |
| 5,467,767 | 11/1995 | Alfano | 128/665 |
| 5,491,524 | 2/1996 | Hellmuth | 351/212 |
| 5,496,305 | 3/1996 | Kittrell | 606/15 |
| 5,507,287 | 4/1996 | Palcic | 128/633 |
| 5,537,162 | 7/1996 | Hellmuth | 351/206 |
| 5,558,669 | 9/1996 | Reynard | 606/15 |
| 5,573,531 | 11/1996 | Gregory | 606/14 |
| 5,591,160 | 1/1997 | Reynard | 606/15 |
| 5,608,520 | 3/1997 | Fleming | 600/478 |

OTHER PUBLICATIONS

Takada, et al, New Measurement System For Fault Location In Optical Waveguide Devices Based On An Interferometric Technique, *Applied Optics*, May 1, 1987, vol. 26 No. 9, pp. 1603–1607.

Fercher, et al., Eye–Length Measurement By Interferometry With Partially Coherent Light, *Optical Society of America*, Mar. 1988, vol. 13, No. 3, pp. 186–188.

(List continued on next page.)

*Primary Examiner*—Ruth S. Smith
*Attorney, Agent, or Firm*—Brian S. Steinberger; Law Offices of Brian S. Steinberger

[57] ABSTRACT

An optical coherence tomography(OCT) and spectral interferometry imaging probe for the automatic screening and diagnosis of cervical and skin cancer in vivo. The probe eliminates the old techniques of having to perform Pap smears followed by a biopsy, known as colposcopy. The novel probe is cylindrical in shape and has a disposable outer plastic shield. Inside the probe is a motor driven rotatable casing having a planar optical fiber bundle array therein. The fiber bundle array has plastic light coupling lenslet arrays on both ends. The exposed end of the probe has one lenslet array disc that couples light between the probe and an interior of the cervix area being examined. Both the casing and the bundle array rotate relative to the outer probe walls. Inside the casing is a rotatable motor driven scanning mirror which couples passes light from an incoming second fiber bundle array to the lenslet array on the inside end of the rotatable casing fiber bundle array. The incoming second fiber bundle array is attached to a detector located external and remote to the probe. The detector has a tunable light source and a spectrometer for providing 3-D images of the interior of the cervix. The proposed technique of simultaneous OCT imaging and spectral interferometry and analysis has potential use in either multi-layer optical disk read out using low coherence tomography and spectral interferometry. Alternatively, by employing spectral interferometry the measured optical spectrum also provides a unique mapping of the recorded bits onto the observed spectral modulation. The unique feature is that by simultaneously employing both spectral interferometry and low coherence tomography, the resultant data transfer rate is increased, but the combination also allows for error rate analysis.

9 Claims, 4 Drawing Sheets

OTHER PUBLICATIONS

Swanson, et al., High–Speed Optical Coherence Domain Reflectometry, *Optics Letters*, Jan. 1992, vol. 17, No. 2, pp. 1864–1865.

Schmitt, et al., Measurement Of Optical Properties Of Biological Tissues By Low–Coherence Reflectometry, *Applies Optics*, Oct. 1993, vol. 32, No. 30, pp. 6032–6042.

Zhou et al., Prospects For Using an Ivem With A Feg For Imaging Macromolecules Towards Atomic Resolution, *Elsevier Science Publishers*, 1993, pp. 408–416.

Hee. et al., Femtosecond transillumination Optical Coherence Tomography, *Optical Society of America*, Jun. 15, 1993, vol. 18 No. 12, pp. 950–952.

Hodson, et al., Detecting Plant Silica Fibres In Animal Tissue By Confocal Fluorescence Microscopy, *Elsevier Science Ltd.*, 1994, vol. 38, No. 2 pp. 149–160.

Bouma, et al., High–Resolution Optical Coherence Tomographic Imaging Using A Mode–Locked Ti:A12 0 3 Lasar Source, *Optical Society of America*, Jul. 1, 1995, vol.$_{13}$, No. 13, pp. 1486–1487.

Brunner, et al., Optical Coherence Tomography (OCT) Of Human Skin With A Slow–Scan CCD–Camera, *SPIE*, vol. 2626, pp. 273–282.

Boppart, et al., Investigation Of Developing Embryonic Morphology Using Optical Coherence Tomography, *Developmental Biology*, 1996, vol. 177, pp. 54–63.

Sergeev, et al., Biomedical Diagnostics Using Optical Coherence Tomography, Brezinski, et al., High Resolution Intraarterial Imaging With Optical Coherence Tomography, Izatt, et al., Optical Coherencetomography And Microscopy In Gastrointestinal Tissues, Coherence Imaging Techniques 1, Mar. 18, 1996, University of Pennsylvania.

Milner, Low Coherence Interferometry as a Biomedical Monitor in Skin, Tearney, et al., High Speed Optical Coherence Tomography, Kulkarni, et al., High Resolution Optical Coherence Tomography Using Deconvolution, Boppart, Optical Coherence Tomography of Embryonic Morphology During Cellular Differentiation, Gleyzes, eta l., a Multichannel Approach to Coherent Optical Imaging Through Turbid Media, Wax, Heterodyne Measurement of Wigner Phase Space Distributions in Turbid Media, Coherence Imaging Techniques 11, Mar. 20, 1996, Russian Academy of Science.

Chan, Imaging Through Biological Tissues by use of Optical Low–Coherence Heterodye Detection Technique, *AMF*, 20, pp. 119–130.

Jones, Real–Time Three Dimensional Imaging Through Turbid Media Using Photorefractive Holography, *AMC*, 4, pp. 27–32.

Maki, Spatial and Temporal Analysis of Human Motor Activity Using Noninvasive Optical Topography, *AMF*, 24, pp. 131–132.

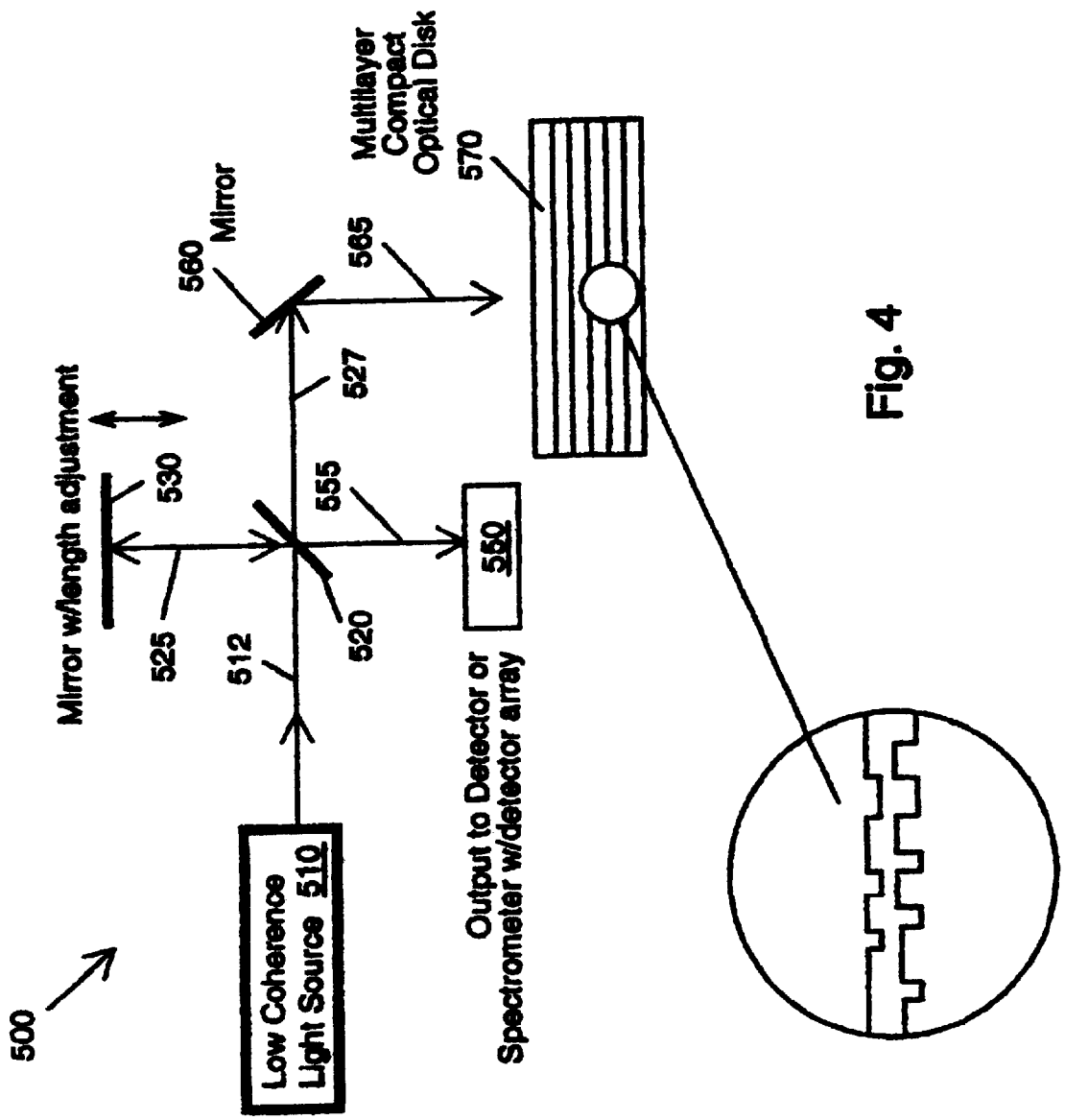

THREE DIMENSIONAL OPTICAL IMAGING COLPOSCOPY

This invention is a Divisional application of U.S. application Ser. No. 09/002,069 filed Dec. 31, 1997, now issued as U.S. Pat. No. 5,921,926 on Jul. 13, 1999, which claims the benefit of Provisional Application 60/053,960 filed on Jul. 28, 1997.

This invention relates to imaging devices, and in particular to a probe that simultaneously performs optical coherence tomography(OCT) and spectral analysis using back reflected light. The probe and attached instrumentation performs three dimensional imaging of cavity interior walls such as but not limited to a uterus/cervix body area for detecting cancerous tumors.

BACKGROUND AND PRIOR ART

Pap smears have been used regularly for diagnosing cervical cancer. Pap smear tests have an approximately 70% sensitivity (true positive/total number of actual abnormal cases). Generally when using a Pap smear for diagnosing cervical cancer, internal tissue areas in the cervix are scraped and analyzed by a microscope to check for abnormal tissues.

Following an abnormal Pap smear, a patient is recommended for a more in depth examination by a gynecologist specializing in cancer, including cancer of the female genital track. Colposcopy (i.e., observation of the cervix) is typically performed on the patient. During colposcopy, a colposcope (a magnifying microscope) is used to attempt to identify suspect lesions. A colposcope image of the cervix is reproduced at a remote distance from the patient. Subsequent to colposcopy, biopsy of suspected lesions is commonly performed for histology follow up. When a biopsy is performed, several tissue samples are cut-out and sent to a cytology laboratory for further analysis. While there are various classifications for degree of cell abnormality, an abnormal lesion can include atypical cells, virus infected cells such as human papilloma, pre malignant cells, and malignant cancer cells.

There are several problems with using the Pap smear first followed by either or both the biopsy and/or the colposcopy. Patient compliance is a major problem to having a biopsy performed. Patients have been known to procrastinate and delay these follow-up procedures because of fear of having a biopsy. This time delay hurts the chance of recovery, since cancer is best treated in its earliest stage. Problems are further compounded because every time abnormal cells are detected during a Pap smear, there has to be another colposcopy and another biopsy. Repeating Pap smears followed each time by colposcopy and biopsy increases the odds of not obtaining patient compliance. Additional problems exist with pregnant patients, because biopsy is not recommended during pregnancy due to the increased risk of bleeding.

Inventions have been proposed for overcoming these problems, but still fail to adequately cover all of these problems with a single procedure. See for example U.S. Pat. Nos. 5,179,937 to Lee; 5,321,501 to Swanson et al.; 5,451, 785 to Faris; 5,458,595 to Tadir et al.; 5,465,147 to Swanson; 5,467,767 to Alfano et al.; 5,491,524 to Hellmuth et al.; 5,496,305 to Kittrell et al.; 5,507,287 to Palcic et al.; 5,537,162 to Hellmuth et al.; 5,558,669 to Reynard; 5,573, 531 to Gregory; and 5,591,160 to Reynard. U.S. Pat. Nos. 5,321,501 and 5,451,785 to Swanson are the closest prior art devices that mention it may be desirable to scan tissue inside tubular structures such as genital tracts. However, these patents do not conduct imaging the spectroscopy simultaneously.

SUMMARY OF THE INVENTION

A primary objective of the present invention is to use a coherence scanning microscope for the diagnosis of surface tissues such as, but not limited to, skin and cervical tissues, in vivo.

The second objective of the present invention is to use optical coherence tomography (OCT) in a probe for three dimensional imaging of a uterus/cervix area for cancer detection.

The third objective of the present invention is to provide a tunable source of low-coherence light to simultaneously conduct spatial imaging and spectral sensing for tissue diagnosis.

The fourth objective of the present invention is to provide real-time three-dimensional colposcopy diagnosis.

The fifth objective of the present invention is to provide an automatic means to guide surgery when cancer has been detected.

The sixth objective of the present invention is to provide guidance to physically biopsy suspicious sites during colposcopy.

Further objects and advantages of this invention will be apparent from the following detailed description of a presently preferred embodiment which is illustrated schematically in the accompanying drawings.

BRIEF DESCRIPTION OF THE FIGURES

FIG. 4 is a schematic view of a third embodiment for optical memory readout using low coherence tomography and spectral interferometry using the detectors of the preceding figures.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
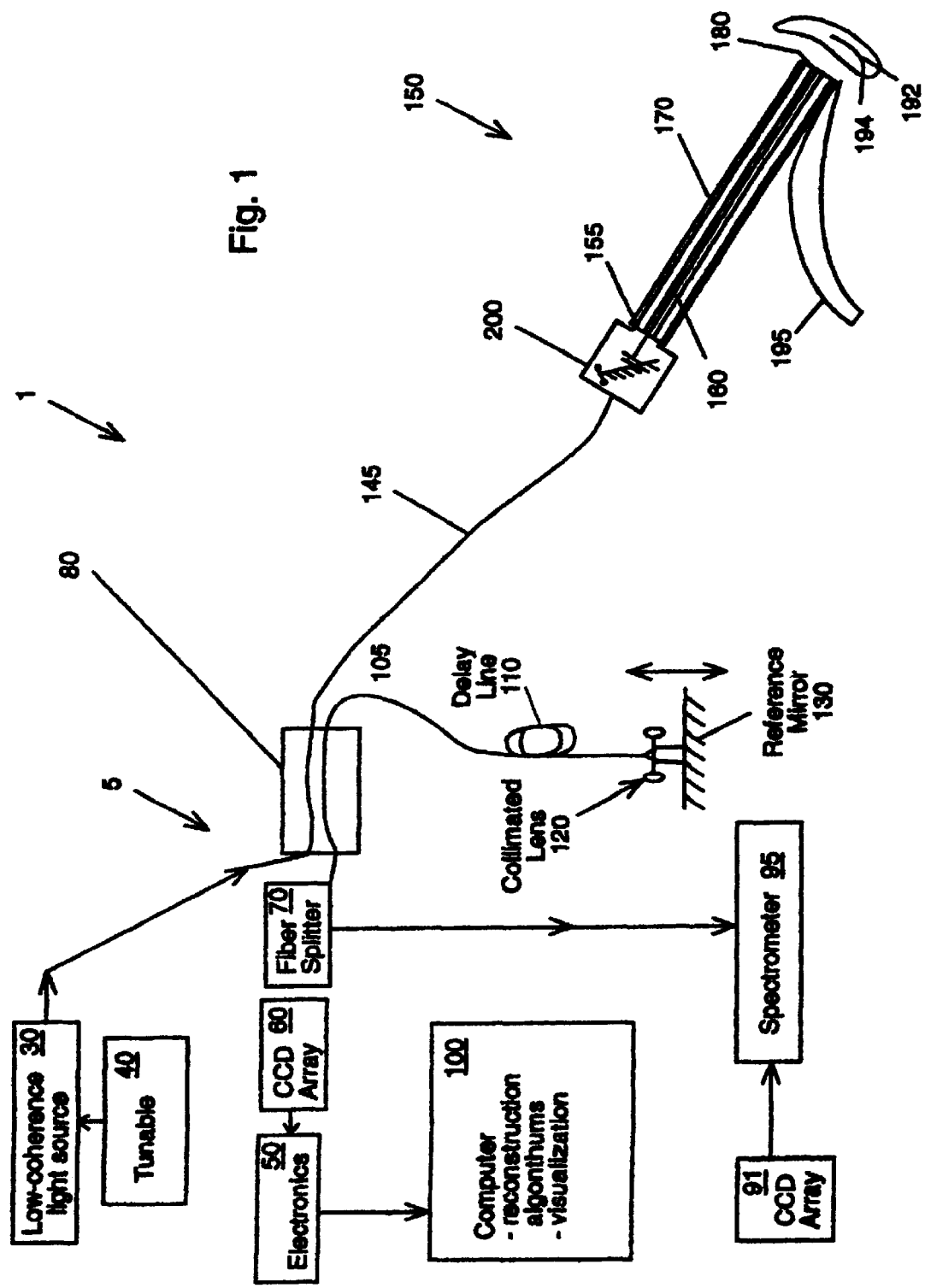
FIG. 1 is a perspective view of a first preferred embodiment of the novel probe and receiver device for simultaneous acquisition of spatial an spectral OCT (SI-OCT).

FIG. 1 is a perspective view of a first preferred embodiment 1 of the novel probe 150 and receiver 5. Each of the components of FIG. 1 will now be described. Fiber splitter 80 can be a 50%/50% fiber splitter such as a JDS Fitel or a Corning component. The low-coherence light source 30 can be continuous or chirped source from emitting diodes(LED), superluminance laser diodes(SLDs), multiple light emitting diode, or a modelocked laser, such as in U.S. Pat. No. 5,469,454 by one of the co-inventors of the subject invention, which is incorporated by reference.

Electronics 50 can be an envelope detector or a demodulation circuit. Detector 60 can be a single detector such as a silicon power meter or a detector array such as a silicon CCD detector array, manufactured by for example, but not limited to Sharp, Toshiba, and NEC. Fiber Splitters 70 and 80 can be a 50%/50% fiber splitter. Spectrometer 95 can be a Jarred-Ashe ¾ meter spectrometer, or an Ocean Optics Spectrometer. CCD Detector 91 can be a linear silicon detector array such as detector 60 manufactured by Sharp, Toshiba, and NEC. Computer 100 can be an IMB586 compatible such as a Dell, Gateway or Compaq computer.

The computer 100 can be used to perform a 3D-image reconstruction from raw or processed data, 3D rendering of reconstructed data, and 3D visualization of rendered data. In the same way that color can be tagged with a saturation parameter and a hue parameter, the amplitude of the back scattered light as well as its spectral signature will serve a tag parameter for the 3D data volume being sensed. OCT imaging can provide the amplitude of the back scattered light at each spatial location (x,y,z), which can be assembled in a 3D matrix that can be displayed as a 3D volume. Software used in computer 100, can be any programming language such as a C, C—, Fortran, IDL, which can visualize the 3D data either as cross sections (x,y) of the tissue or as a volume using various visualization techniques such as transparency rendering, volume rendering, and the like. Similarly, the spectral data can be visualized separately and one or several parameters from the spectral analysis can be extracted. Those parameters can also serve as a tag to the spatial data. Moreover, spectral data can be used in processing the spatial data as data provides information about the dispositives of the medical condition. Finally, data fusion of spatial and spectral information can be performed as yet another way to visualize the data.

Delay line 110 can be an adjustable optical delay using a stepper motor and optical flat or retroreflecting mirror, or microreflector sheet, a mirror made of reflector tubes, or an helicoid rotating mirror, or an expanding fiber optical cylindrical solenoid. The collimated lens 120 can be a fiber optical collection lens cemented or not to the fiber with for an example, a 0.1 numerical aperture or equivalently an F-number of 5. The reference Mirror 130 can be a flat silver, gold, or dielectric mirror manufactured by Newport for example. Single mode fiber 145 is an approximately 5 micron to approximately 10 micron core optical fiber with optional polarization preserving. Under polarization preserving light entering the optical fiber with a given state of polarization (such as vertically polarized) exits from the optical fiber with the same state of polarization (i.e. vertically polarized).

Figure 2:
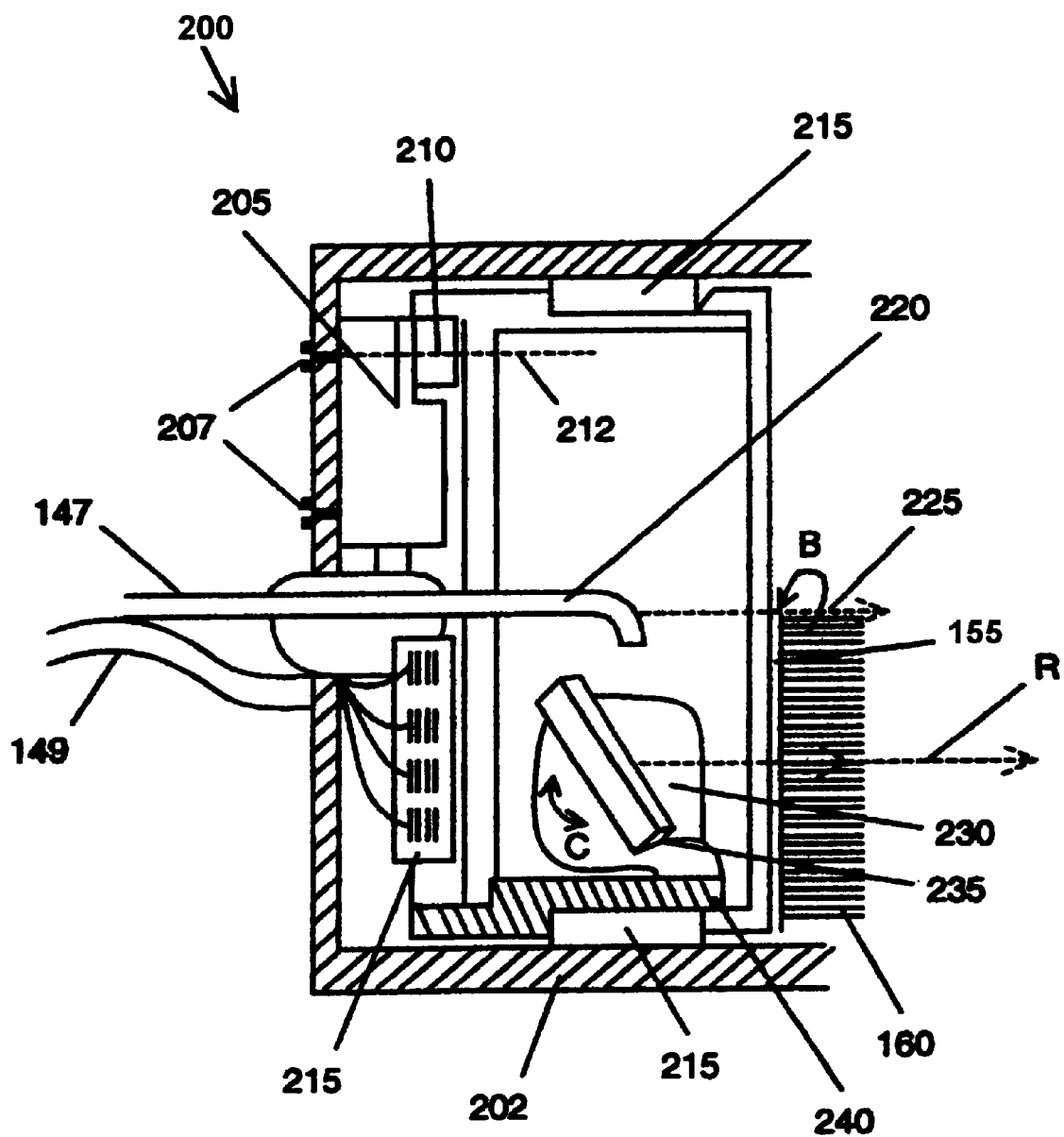
FIG. 2 is an enlarged view of the rear portion of the probe of FIG. 1.

Referring to FIG. 1, axially rotating probe 200 includes a scanning mirror and the fiber optics array, and a lenslet array, shown in more detail in reference to FIG. 2. Optoelectronics scanners providing random access scanning acousto-optics scanners, can also be used instead of a mirror. Plastic lenslet array 155 can have an approximately 0.1 numerical aperture and approximately 200 micron center to center spacing. Planar fiber optics array 160 is a coherent linear fiber bundle in one plane where a multiplicity of optical fiber is laid down, one by one next to each other forming one layer or one plane. A disposable plastic envelope 170 encompasses optics array 160, and a disposable sealed plastic lenslet array 180 such as that described in reference to 155 is across the front face of envelope 170.

A speculum 195, currently used in medical practice to do either a Pap smear or colposcopy, such as the one described in U.S. Pat. No. 5,179,937, which is incorporated by reference, is used for vaginal inspection, so that probe 200 can allow for imaging of the endocervical canal 192 and the face of the cervix 194.

FIG. 2 is an enlarged cross-sectional view of the rear portion 200 of the probe 150 of FIG. 1. Incoming optic fiber 147 from main receiver 5 is shown in FIG. 1. Referring to FIG. 2, electrical wire bundle 149 can be a group of electrical wires which carry current for powering servo motor 230. An outer casing 202 such as an aluminum box can contain the probe-optical scanning components. Screw type fasteners 207 fasten DC servo motor 205 to the casing 202, and motor head gear 210 allows cylinder 240 to rotate within casing 202. Cylindrical bearings 215 are a metal type cylinder that prevents the translation of the probe 200. A single mode optical fiber 220 extends into the interior of probe 200. Cylinder 240 lens array 155 and planar optical fiber array 160 rotates in the direction or counter direction of arrow B about the central axis of rotation 225. Servo motor 230 can be another DC servo motor similar in operation to motor 205 described above. Mirror 235 can be a metal or dielectric highly reflecting mirror, and the rotating cylinder 240 can be a hollow metal cylinder.

The above described components allow for simultaneous OCT and spectral imaging for cancer diagnosis of the cervix. Because of the low coherence of the light source used for OCT imaging, back scattered light only interferes constructively, that is adds, when the optical path length difference between the light path to the reference mirror 130, and that to the sample 192, 194 is less than the coherence length of the light. Therefore, as the optical path length to the mirror shortens or expands as a result of the z-scan done by the reference mirror 130 in our embodiment, the image depth in the tissue that can produce constructive interference with the reference path is that for which the optical path length is equal to the referenced beam with a precision of the coherence length of the light source. Scan can be performed by various scanning schemes including a moving mirror 235 rotatable in the direction of arrow C or expending piezoelectric solenoid on which the optical fiber is enrolled. Typically, resolutions in z of 10–13 microns can be achieved with current OCT systems. While this interferometric principle, which is nothing more than the Michelson interferometer principle first demonstrated in the 1800's which, in its utilization for biological tissue sensing, one must operate at a wavelength or a set of wavelength where the tissue is transparent to the light, meaning there is little or no absorption. The fundamental principle has also been referred as an coherent microscope principle before OCT was named as such. The subject invention uses a broad spectrum wavelengths from 0.4 $\mu$m to 1.3 $\mu$m. For the spectral analysis, various wavelength can be used depending on the type of analysis. For spectral interferometry, visible or infrared light can be used. For fluorescence spectroscopy, one will also want to operate in part in the blues, at approximately 0.4 $\mu$m.

Figure 3:
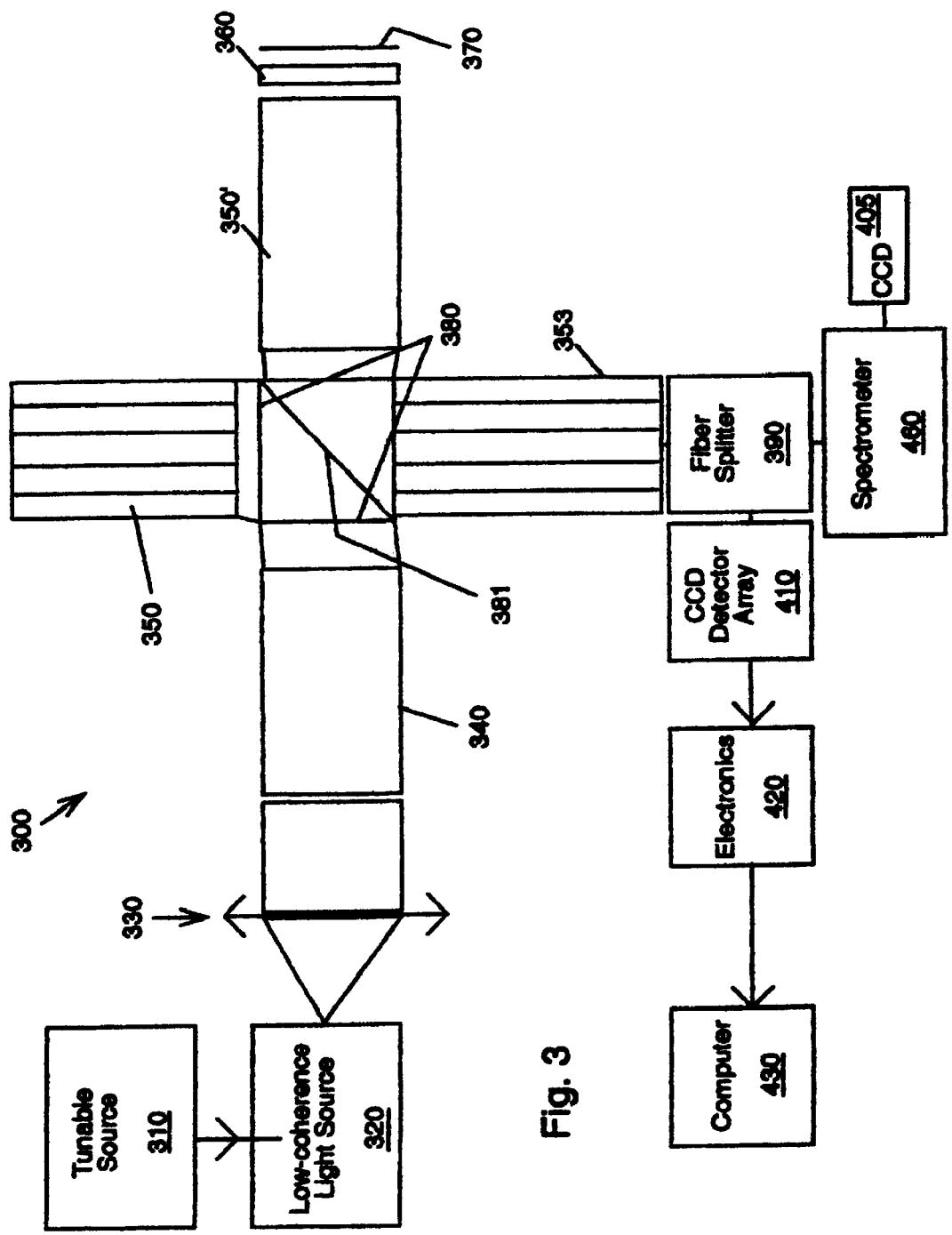
FIG. 3 is a perspective view of a second embodiment of a SI-OCT interferometer and parallel detector acquisition system used with the probe of FIG. 1.

FIG. 3 is a perspective view of a second embodiment 300 of a interferometer and parallel detector acquisition system used with the probe of FIG. 1. The components of FIG. 3 will now be described. Tunable low coherent optical source 310 can be a spectrally broad band light, LED, modelocked laser or chirped pulse light source. The low coherence light source 320 can be a light emitting diode or equivalent type source. Collimating lens 330 and 360 can be positive lens (plastic glass) or lenslit array. Collimating lens 330 is used to collimate light from light source 310 and 320. Collimating lens 360 is used to collimate light impinging on the reference mirror 370 back into the fiber 350'. Fiber optic bundles 340, 350, and 350' can be 2-D coherent fiber bundles. Reference mirror 370 is similar to reference mirror 235 described previously. Reference Mirror 370 can be replaced by a micro-lenses of retro-reflectors, or other types of mirrors such as those described previously, for redirecting light. The light coupling lenslit arrays 380 can be a micro lenses arranged in a 2-D array to collect and collimate light to beam splitter 381. Fiber splitter 390 can be a 50%/50% fiber splitter that directs light to a CCD detector array 410(similar to detector 60 previously described) and to the spectrometer 400(similar to 95 previously described). Electronics 420 is equivalent to previously described electronics 50 which can be an envelope detector, a demodulator circuit, and the like. Computer 430 is equivalent to computer 100 described previously.

In this configuration of incorporating FIG. 3 into the probe 200 of FIG. 2, the light source is collimated and fed in parallel to the fiber optic bundle 340. Upon exiting fiber 340, the light is coupled into the fiber bundles 350 and 353 via lenslet arrays glued to the beam splitter 381. On the reference path, the light exiting the bundle array 350 is collimated before it is reflected by the reference mirror 370. Upon reflection, the light is coupled back to the same fiber bundle 350. It is then reflected at the half silvered surface of the beam splitter 381 which corresponds to the diagonal line in the middle of element 381. The light is then directed using fiber bundle 353 (the one going down) in part to the CCD detector array 405 and in part to the spectrometer 400. On the sample path, the light reflected upward (in this case) the beam splitter goes to the in vivo biological tissue to be diagnosed. Light is reflected back in parallel from the surface of the tissue and all layers of the tissue, but only the tissue at the depth corresponding to the equivalent optical path for the reference beam will be detected. This configuration allows parallel processing on information. Because of the limitation in resolution of current technology fibers, samples separated 100 to 200 micron apart are imaged simultaneously. By allowing transversal scan of the overall probe assembly resolution to sub fiber sizes can be obtained. If fibers are separated by 100 microns, for example, 10 transversal scan values can allow 10 microns transversal resolution. With nonotechnology of the future no transversal scan will be necessary.

FIG. 4 is a schematic view of a third embodiment 500 for optical memory readout using low coherence tomography and spectral interferometry using the detectors of the preceding figures. Embodiment 500 encompasses a multi-layer optical disk readout using low coherence tomography and spectral interferometry. The concept of optical disk readout using OCT, or optical coherence tomography is similar to that employed in imagining techniques. The salient feature is to measure the cross-correlation function from the reflected light returning from a multilayer compact optical disk. The locations of the peaks in the correlation function uniquely determine the bit pattern recorded on the optical disk as a function of depth within the disk. Alternatively, by employing spectral interferometry, the measured optical spectrum also provides a unique mapping of the recorded bits onto the observed spectral modulation. The unique feature is that by simultaneously employing both spectral interferometry and low coherence tomography, the resultant data transfer rate is increased, and the combination also allows for error rate analysis. Similarly for medical diagnosis, combining OCT and spectral OCT or spectroscopy will for higher sensitivity and specificity than obtained or either method alone.

Referring to FIG. 4, embodiment 500 includes a low coherence light source 510. Low coherence light source 510 can be an LED or superluminescent laser diode having a wavelength of approximately 830 nm. Component 520 can be a partially silvered mirror or a beam splitter. Mirror 530 and 560 with length adjustment can be a dielectric or metal highly reflective mirrors. Detector or spectrometer with detector array 550 can be a Jarred Ashe spectrometer and linear silicon diode detector array. Multilayer compact optical disk 570 can be a layered dielectric mirror with recorded pits and lands.

The low coherent light source 510 generates the light to be used in the low coherence memory application. The light is collected and collimated and directed to a 50%/50% beam splitter 520. The two beams generated from the beam splitter are directed to a mirror 530, 560 with a length adjustment and to the multilayer compact optical disk. Light is reflected from the mirror 530, 560 with length adjustment and the compact optical disk. It should be noted that owing to the separate, individual layers within the optical disk, a portion of the light is reflected from each layer. The reflected light from both the movable mirrors 530, 560, and from each layer within the compact optical disk 570 is recombined back on the beam splitter 520. The recombined light 555 is then measured using a detector or spectrometer 550 with a detector array. By adjusting the optical path length using the movable mirror, the resulting interference, or correlation function, is measured. It should be noted that each peak in the correlation function provides information as to whether there is a recorded pit or land, corresponding to a logical 1 to 0, at a specific location on the optical disk. Alternatively, by measuring the spectral interference fringe pattern using the spectrometer and the detector array 550, the spectral pattern yields a unique distribution which corresponds to the data bits recorded at each level in the disk at a specific location.

By collecting the correlation, or spectral interferometry, data at each position on the multilayer optical disk 570, one extracts the data recorded at each location and on each layer within the optical disk.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An Optical Coherence Tomography(OCT) and spectral interferometry probe for image scanning and parallel processing of information, comprising in combination:

a cylindrical probe for being inserted into a cavity;

collimating means for forming parallel light;

an optical imaging means having an optical fiber bundle array mounted within the probe for optically scanning an interior portion of a cavity with the parallel light which is reflected back in parallel from the interior portion of the cavity; and a spectrometer detector remotely attached to the probe for providing a spectral analysis image of the parallel reflected light from the optical scanning of the interior portion of the cavity.

2. The optical coherence tomography(OCT) and spectral interferometry probe of claim 1, wherein the optical fiber array includes:

an optical fiber planar array.

3. The optical coherence tomography(OCT) and spectral interferometry probe of claim 1, wherein the optical imaging means further includes:

a rotatable case within the probe for housing the optical fiber array.

4. The optical coherence tomography(OCT) and spectral interferometry probe of claim 1, further comprising:

a tunable light source and a low-coherence light source for emitting light to the collimating means.

5. The optical coherence tomography(OCT) and spectral interferometry probe of claim 1, the optical imaging means further includes:

a nonmoving reference mirror; and a second collimating means for collimating light from the nonmoving reference mirror.

6. An Optical Coherence Tomography(OCT) and spectral interferometry probe and detector for image scanning and parallel processing of information, comprising in combination:

collimating means for forming a parallel light source;

a cylindrical probe for being inserted into a cavity;

an optical imaging means having an optical fiber array mounted within the probe for optically scanning an interior surface in the cavity with the parallel light source which is reflected back in parallel from the interior surface; and a spectrometer detector attached to the probe for providing a spectral analysis image of the parallel reflected light from the optical scanning of the interior the surface.

7. The Optical Coherence Tomography(OCT) and spectral interferometry probe and detector of claim 6, further comprising:

a rotatable case for housing the optical imaging means.

8. The Optical Coherence Tomography(OCT) and spectral interferometry probe and detector of claim 6, further comprising:

a tunable light source and a low-coherence light source for emitting light to the collimating means.

9. The Optical Coherence Tomography(OCT) and spectral interferometry probe and detector of claim 6, the optical imaging means further includes:

a nonmoving reference mirror; and a second collimating means for collimating light from the nonmoving reference mirror.

* * * * *